(12) United States Patent
Sommer et al.

(10) Patent No.: US 8,740,952 B2
(45) Date of Patent: *Jun. 3, 2014

(54) HYBRID PLATE SYSTEM AND METHOD

(71) Applicant: Stryker Trauma SA, Selzach (CH)

(72) Inventors: Thomas Sommer, Ostermundigen (CH); Philip Henry, Biel/Bienne (CH)

(73) Assignee: Stryker Trauma SA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/722,264

(22) Filed: Dec. 20, 2012

(65) Prior Publication Data

US 2013/0110175 A1 May 2, 2013

Related U.S. Application Data (63) Continuation of application No. 12/316,661, filed on Dec. 15, 2008, now Pat. No. 8,343,198.

(60) Provisional application No. 61/008,374, filed on Dec. 20, 2007.

(51) Int. Cl.
*A61B 17/88* (2006.01)

(52) U.S. Cl.
USPC ............................ 606/281; 606/291; 606/76

(58) Field of Classification Search
USPC ................ 606/70, 280, 281–299, 76, 71, 321
See application file for complete search history.

(56) References Cited

U.S. PATENT DOCUMENTS

| | | | |
|---|---|---|---|
| 5,931,838 A | | 8/1999 | Vito |
| 6,056,751 A | * | 5/2000 | Fenton, Jr. ...................... 606/28 |
| 6,955,677 B2 | | 10/2005 | Dahners |
| 7,048,739 B2 | | 5/2006 | Konieczynski et al. |
| 7,175,624 B2 | | 2/2007 | Konieczynski et al. |
| 2004/0030341 A1 | * | 2/2004 | Aeschlimann et al. .......... 606/72 |
| 2006/0116678 A1 | | 6/2006 | Impellizzeri |

* cited by examiner

*Primary Examiner* — Andrew Yang
(74) *Attorney, Agent, or Firm* — Lerner, David, Littenberg, Krumholz & Mentlik, LLP (57) ABSTRACT

A bone plate system is disclosed which includes a bone plate having at least one plate hole, at least one pin adapted to be disposed in the at least one plate hole, and a polymer component disposed between the at least one pin and the bone plate. The polymer component includes a polymer that may be melted through the application of ultrasonic energy. The at least one pin is constructed of a material that will not melt under such application of ultrasonic energy. The re-solidified polymer component creates a bond between the at least one pin and the bone plate to provide a more rigid and secure mating therebetween, and to at least substantially prevent backout of the at least one pin with respect to the bone plate. A method of implanting the bone plate system is also disclosed.

23 Claims, 7 Drawing Sheets

HYBRID PLATE SYSTEM AND METHOD

CROSS-REFERENCE TO RELATED APPLICATIONS

The present application is a continuation of U.S. patent application Ser. No. 12/316,661, filed on Dec. 15, 2008, which claims the benefit of the filing date of U.S. Provisional Patent Application No. 61/008,374 filed Dec. 20, 2007, the disclosures of which are hereby incorporated herein by reference.

BACKGROUND OF THE INVENTION

The present invention relates to a bone plate system, and more particularly, to an improved hybrid bone plate system including a screw at least partially covered with a polymer component that is inserted into the bone plate to achieve a secure fit.

Locked plating techniques offer an alternative biomechanical approach for fracture fixation. Locking screw-plate systems act as single-beam constructs in the bone, and the plate does not require compression and friction generation to achieve mechanical stability. In locked plating systems, screws or pins with threads on the undersurface of the head are threaded into the plate, creating a fixed-angle device that does not allow screw toggle. Current clinical problems with such systems include: loosening of screw-plate connections; breakage/deformation of screw-plate connections; time consuming screw insertion; breakage/deformation of screws or blades in surgeries; and explantation/material removals. Undesirable loss of screw purchase in some conventional systems is related to the failure of fixation systems in osteoporotic bone or other weakened bone. Therefore, there is a need for an improved bone plate system.

BRIEF SUMMARY OF THE INVENTION

In accordance with the present invention, these and other objections have been met by the invention of a bone plate system comprising a bone plate including at least one plate hole formed in the bone plate, at least one pin having a head and a shaft and adapted to be disposed in the at least one plate hole, and a polymer component disposed between the at least one pin and the bone plate, wherein the polymer component is made at least in part of a polymer which may be melted through the application of ultrasonic energy. In a preferred embodiment, the at least one pin comprises a material that will not be melted through the application of the ultrasonic energy. Preferably, the material comprises a polymer, and more preferably it comprises a metal.

In accordance with one embodiment of the bone plate system of the present invention, the polymer component comprises a coating applied to the head of the at least one pin. In another embodiment, the polymer component comprises a coating applied to the shaft of the at least one pin. In yet another embodiment, the polymer component comprises an insert disposed about the head of the at least one pin. Preferably, the insert has an exterior surface configured to be substantially similar in shape to the exterior surface of the head of the at least one pin.

In accordance with another embodiment of the bone plate system of the present invention, the polymer component is constructed to bond the at least one pin to the bone plate. In one embodiment the at least one plate hole includes at least one helical ridge. In another embodiment the at least one plate hole includes a series of concentric ridges adjacent to one another. Preferably, the head of the at least one pin includes at least one ridge.

In accordance with another embodiment of the bone plate system of the present invention, the at least one plate hole in the head of the at least one pin each includes tapered surfaces such that the at least one plate hole substantially mates with the head of the at least one pin, and the polymer component is disposed between the tapered surfaces of the at least one plate hole and the head of the at least one pin.

In accordance with another embodiment of the bone plate system of the present invention, the shaft is threaded. In another embodiment, the head of the at least one pin further includes a projection disposed opposite the shaft, the projection being configured to mate with an implantation tool.

In accordance with another embodiment of the bone plate system of the present invention, the bone plate and the pin comprise biocompatible metals. In another embodiment, the pin comprises a biocompatible ceramic. In yet another embodiment, the at least one plate hole includes a lateral groove. In another embodiment the head of the at least one pin includes a lateral groove. In a preferred embodiment, the at least one pin comprises a self-tapping screw.

In accordance with the present invention, a method of implanting a bone plate system has been discovered comprising the steps of positioning a bone plate adjacent to a fracture in a bone, the bone plate having at least one plate hole formed therein, inserting a pin through the at least one plate hole and into a hole in the bone, providing a polymer component between at least the pin and the bone plate, melting the polymer component through the application of energy, and allowing the polymer component to re-solidify such that a bond is formed between the bone plate and the pin. Preferably, the melting step includes the application of ultrasonic energy. In a preferred embodiment, the inserting step includes the use of a driving force applied to the pin.

In accordance with one embodiment of the method of the present invention, the method includes pre-drilling the hole in the bone using a guide. In a preferred embodiment, the method includes pre-drilling the hole in the bone using the bone plate as the guide.

In accordance with another embodiment of the method of the present invention, the pin comprises a self-tapping screw.

The bone plate used in the bone plate system of the present invention is used to maintain bone fragments in a rigid orientation while the bone heals. The present hybrid plate system and methods achieve such a result. The hybrid plate system consists of a bone plate, at least one pin, and a polymer component. The polymer component not only forms a strong bond between the at least one pin and the bone plate, but also provides enhanced stability between the at least one pin and the adjacent bone.

In use, in one aspect of the present invention, a pin and a polymer component are inserted through at least one plate hole in the bone plate and into the bone. The pin is driven using a force and ultrasonic energy which melts the polymer component between the pin and the bone plate and/or the pin and the bone. The polymer component forms a bond between the pin and the bone plate and/or the pin and the bone in order to provide a complete and rigid connection.

DETAILED DESCRIPTION

Figure 1:
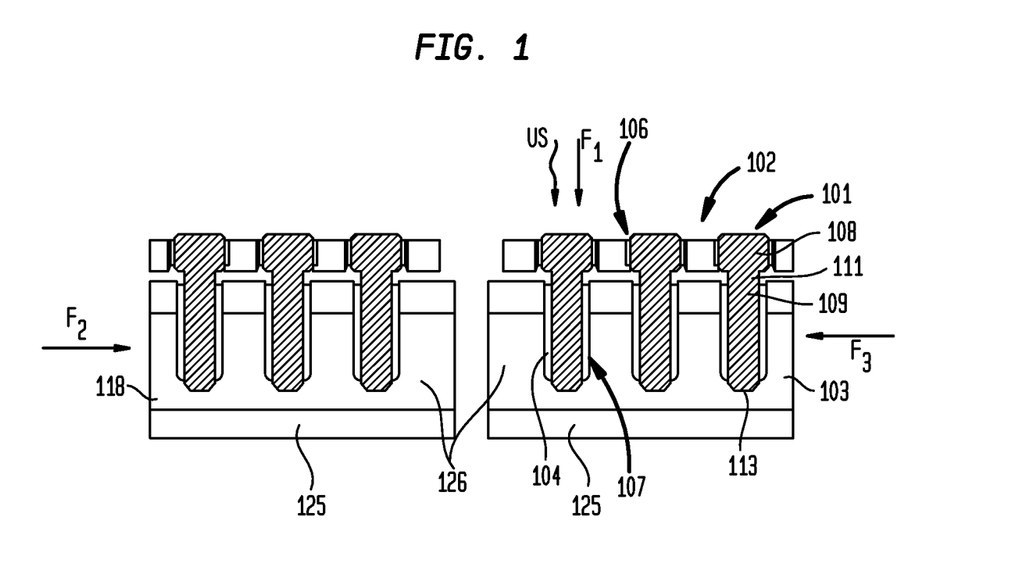
FIG. 1 is a cross-sectional view of a bone plate secured to a bone according to an embodiment of the present invention.
Figure 2:
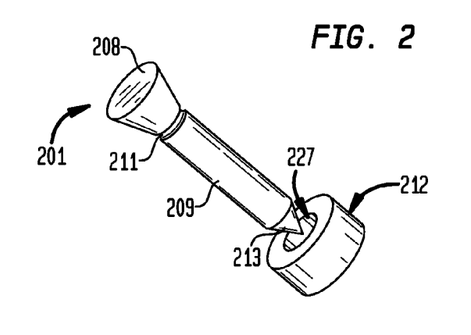
FIG. 2 is a front perspective view of a pin and a polymer component according to another embodiment of the present invention.
Figure 3:
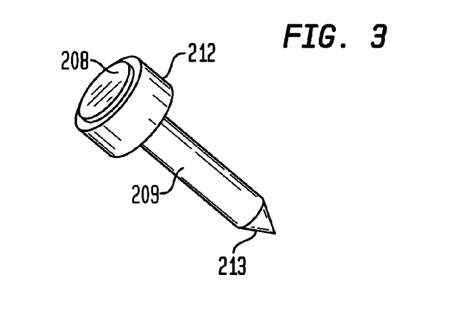
FIG. 3 is a front perspective view of the pin and the polymer component shown in FIG. 2 in an assembled state.

FIG. 1 depicts a first exemplary embodiment of a hybrid plate system securing two bone fragments 103 and 118 together via a plurality of pins 101. In FIG. 1, pins 101 are depicted as being unthreaded, although pins according to the present invention may also be threaded. The hybrid plate system includes at least one pin 101 and a bone plate 102 that contains at least one plate hole 106. Bone plate 102 may be comprised of any biocompatible rigid material, for example, biocompatible metal. Pin 101 includes a head 108, a shaft 109, a neck 111, and a tip 113. Pin 101 may be comprised of any biocompatible rigid material, and is preferably comprised of a material that will not be melted through the application of ultrasonic energy. Such a material may be a polymer, metal, ceramic, etc. Of course, if pin 101 is comprised of a polymer, it is preferable that such a polymer not be susceptible to melting when an ultrasonic energy is applied. Thus, the polymer comprising pin 101 would be of a different composition than that of a polymer component 104, which is more fully described below. In another embodiment, pin 101 may include threads on shaft 109 so that pin 101 may be threaded into one or more bone fragments. Head 108 is sized to correspond with plate hole 102, though an exact mating is not necessary or required.

Disposed on pin 101 is polymer component 104, which may entirely or partially cover the surface of pin 101. Polymer component 104 can take on many forms, such as a coating, layer, insert, ring, etc. For example, pin 101 may be coated with polymer component 104 prior to implantation, or polymer component 104 may be provided as an insert or ring at the time of implantation. No particular form of polymer component 104 is known to provide any advantage. Rather, polymer component 104 is comprised of a polymer that melts under the application of an ultrasonic energy.

Prior to use of the hybrid plate system, bone fragments 103 and 118 are oriented in a manner so as to be rigidly set. One or more bone holes 107 may be drilled prior to the insertion of pins 101 by using bone plate 102 as a guide. Alternatively, bone holes 107 may be drilled using a separate guide or template. In yet another embodiment, pin 101 may be a self-tapping screw. Bone holes 107 preferably extend through the cortical portion 125 of bone fragments 103 and 118 and into the cancellous portion 126 of the bone. It is preferable that the dimensions of bone hole 107 closely approximate the dimensions of at least a portion of pin 101 so that a mating fit may be established therebetween, though an exact mating is not necessary or required.

After bone holes 107 are formed in bone fragments 103 and 118, bone plate 102 is positioned adjacent to bone fragments 103 and 118 so that plate holes 106 are aligned with the bone holes 107. Pins 101 are then inserted through plate holes 106 and into bone holes 107 to secure bone plate 102 to bone fragments 103 and 118, thereby positioning bone fragments 103 and 118 relative to one another and prevent movement therebetween. Pins 101 are inserted through the use of force $F_1$ and ultrasonic energy US. Force $F_1$ is preferably aligned with the axis of shaft 109 in order to driving pin 101 through plate hole 106 and into bone hole 107. In addition, ultrasonic energy US may be simultaneously applied with force $F_1$ so as to melt polymer component 104, which subsequently re-solidifies to provide a rigid bond and a more secure and exact mating between pin 101 and bone plate 102 and/or pin 101 and bone hole 107. Polymer component 104 substantially fills the space between pin 101 and bone plate 102 and/or pin 101 and bone hole 107. At least one pin 101 may be inserted into each of the bone fragments 103 and 118 to provide a rigid and stable connection between bone plate 102 and bone fragments 103 and 118.

FIGS. 2 through 5 depict another embodiment of a hybrid plate system having a pin 201 and a polymer component 212 for insertion into bone plate 202 and one or more bone fragments. Polymer component 212 is in the form of a ring and has a polymer component hole 227. Pin 201 has a head 208, a shaft 209, a neck 211, and a tip 213. Polymer component 212 is configured in an annular arrangement, though any arrangement which allows shaft 209 to pass through polymer component 212 may be used. Shaft 209 is inserted into polymer component hole 227 until polymer component 212 is disposed about head 208. Polymer component 212 may be attached to pin 201 ultrasonically prior to insertion and attachment of pin 201 to bone plate 202. Head 208 is conical and tapered, having a smaller diameter adjacent to neck 211 and a larger diameter opposite neck 211. Polymer component hole 227 may be tapered to match the tapering of head 208. The tapered configuration of head 208 allows polymer component 212 to slide onto head 208.

Figure 4:
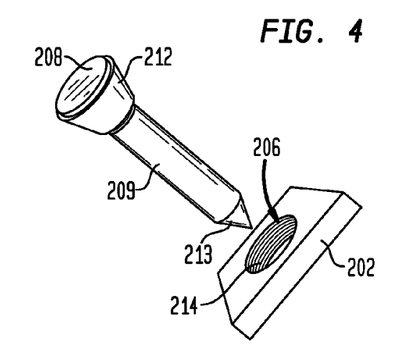
FIG. 4 is a front perspective view of the pin and the polymer component shown in FIG. 2 with a bone plate.
Figure 5:
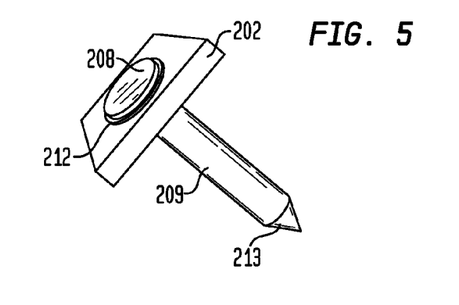
FIG. 5 is a front perspective view of an assembly of the pin, the polymer component, and the bone plate shown in FIG. 4.
Figure 6:
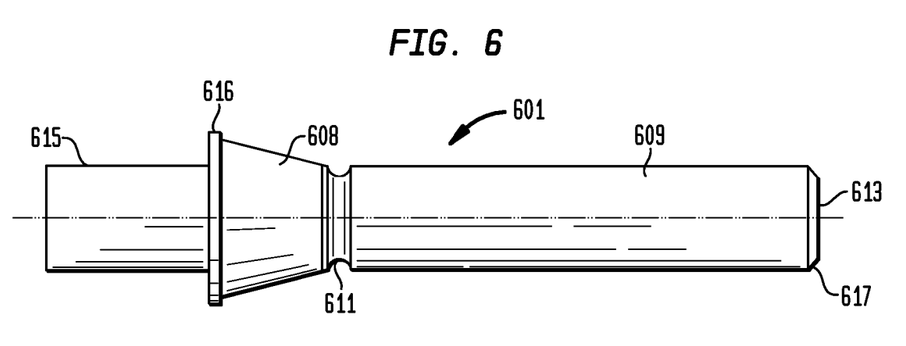
FIG. 6 is a side view of a pin according to another embodiment of the present invention.
Figure 7:
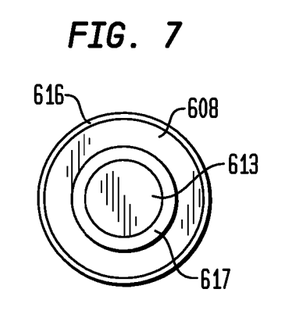
FIG. 7 is an end view of the pin shown in FIG. 6.
Figure 8:
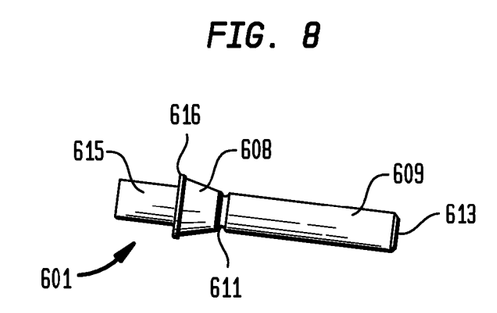
FIG. 8 is a side perspective view of the pin shown in FIG. 6.
Figure 9:
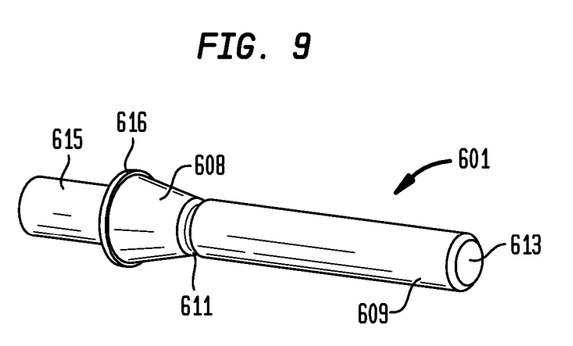
FIG. 9 is another side perspective view of the pin shown in FIG. 6.

Either before or after its assembly with pin 201, polymer component 212 may be machined or otherwise modified into a configuration which more approximately resembles the tapering of head 208 and the configuration of a tapered plate hole 206. Such a configuration is shown in FIG. 4. It is noted that bone plate 202 may be configured as shown in FIG. 4, or it may be taken as a section of a larger plate having two or more plate holes 206. The inside of plate hole 206 may include plate hole ridges 214, striations, or other machined features to assist in fixation of the polymer component to plate hole 206. Plate hole ridges 214 may be a series of circumferential and concentric ridges adjacent to one another. Plate hole ridges 214 may alternatively be designed in a threadedfashion whereby plate hole ridges 214 form one continuous winding, spiral, or helical plate hole ridge 214. The purpose of plate hole ridges 214 is to provide crests and valleys on the mating surface of plate hole 206 with which polymer component 212 and head 208 can mate, thereby further preventing or at least substantially hindering backout of pin 201 with respect to bone plate 202. After shaft 209 is inserted through plate hole 206, polymer component 212 contacts plate hole ridges 214. Application of ultrasonic energy US melts polymer component 212 so that polymer component 212 conforms to plate hole ridges 214 in plate hole 206 thereby forming a secure fit between pin 201 and bone plate 202, as shown in FIG. 5. Pin 201 may also include a polymer component on shaft 209 which would also be melted by ultrasonic energy US at the bone interface to form a bond between pin 201 and the bone.

Another embodiment of the present invention is depicted in FIGS. 6 through 15. As shown in FIGS. 6 through 9, a pin 601 has a head 608, a shaft 609, and a neck 611. Shaft 609 has a tip 613 and a tapered edge 617. Head 608 has a lip 616 positioned at the end of head 608 opposite neck 611. Extending from head 608 opposite shaft 609 is a projection 615 which may be used during insertion of pin 601 into a bone plate, to position pin 601 thereafter, or for any other manipulative purpose. Projection 615 may be configured to receive an implantation tool, such as an ultrasonic energy applicator and/or driving tool. Of course, projection 615 may be removed from pin 601 after implantation. Tip 613 is shown, about which is disposed tapered edge 617.

Figure 10:
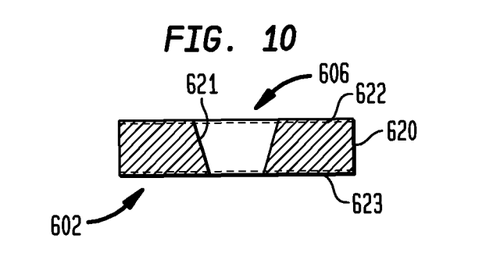
FIG. 10 is a side cross-sectional view of a bone plate according to another embodiment of the present invention.
Figure 11:
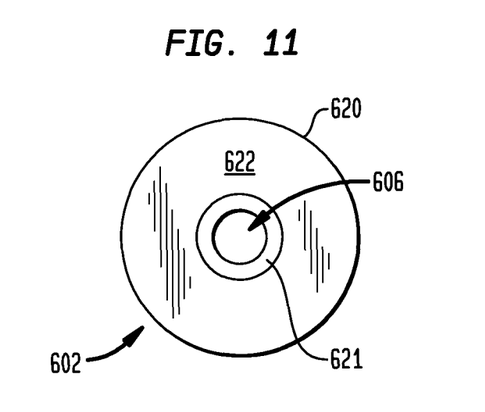
FIG. 11 is a top view of the bone plate shown in FIG. 10.
Figure 12:
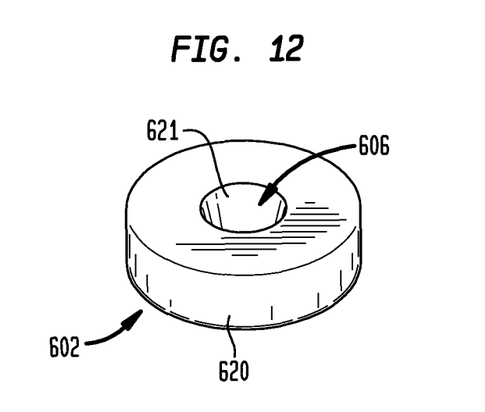
FIG. 12 is a top perspective view of the bone plate shown in FIG. 10.

FIGS. 10 through 12 depict a bone plate 602, which alternatively may be understood to be a portion of a larger bone plate. Bone plate 602 comprises a plate hole 606 and an outer edge 620. Of course, it is within the scope of the present invention to provide a bone plate similar to that depicted in FIGS. 10 through 12 but including two or more plate holes 606 as desired. The configuration of such a bone plate may be of any size and shape to appropriately fit the bone or bones to which it is to be anchored. Plate hole 606 has a tapered wall 621, such that plate hole 606 is wider near an upper surface 622 of bone plate 602 and narrower near a lower surface 623 of bone plate 602. Outer edge 620 of bone plate 602 is substantially annular in shape, but can take on any other suitable shape, such as square, rectangular, triangular, etc.

Figure 13:
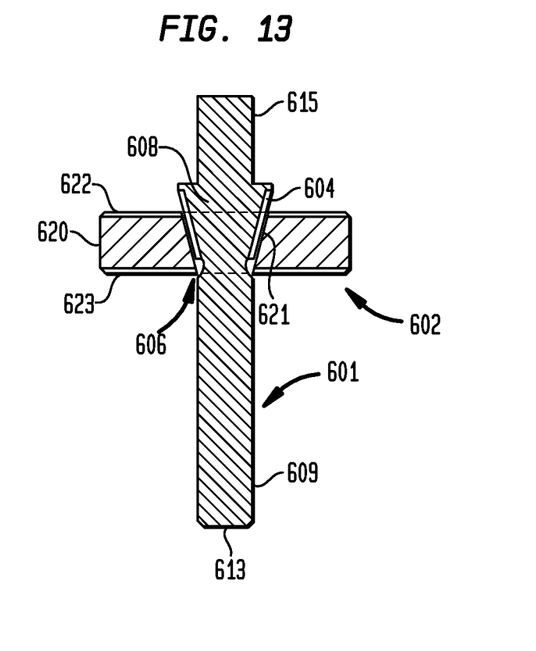
FIG. 13 is a side cross-sectional view of the pin shown in FIG. 6 assembled with the bone plate shown in FIG. 10.
Figure 14:
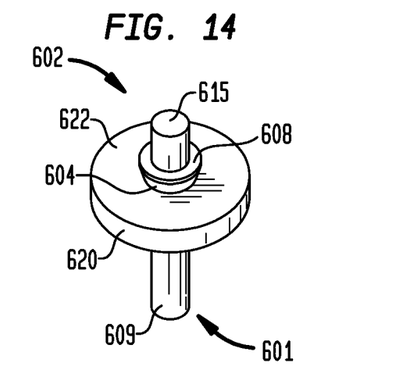
FIG. 14 is a top perspective view of the assembly shown in FIG. 13.
Figure 15:
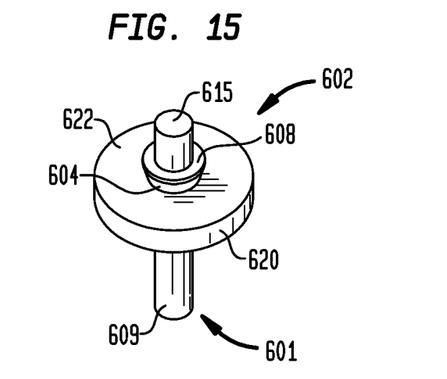
FIG. 15 is another top perspective view of the assembly shown in FIG. 13.

FIGS. 13 through 15 depict bone plate 602 mated with pin 601. Pin 601 is positioned through plate hole 606 such that head 608 is positioned against tapered wall 621. Head 608 is of a generally tapered orientation so that tapered wall 621 and head 608 mate to form a substantially tight fit. Disposed between plate hole 606 and head 608 is polymer component 604.

Figure 16:
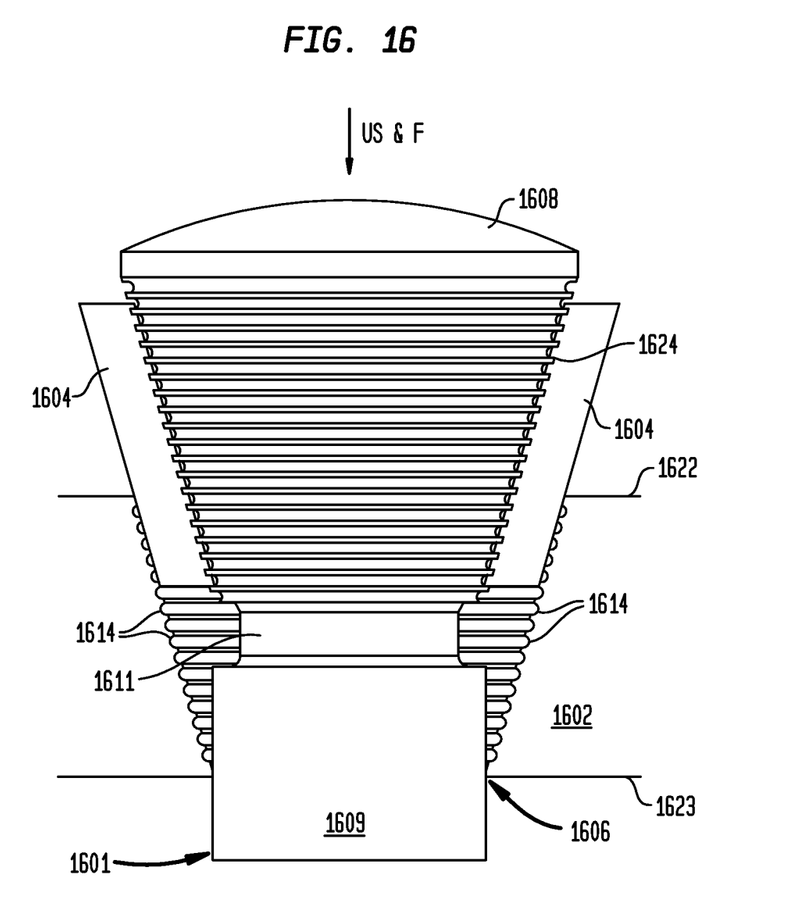
FIG. 16 is a side cross-sectional view of a pin during insertion into a bone plate according to another embodiment of the present invention.
Figure 17:
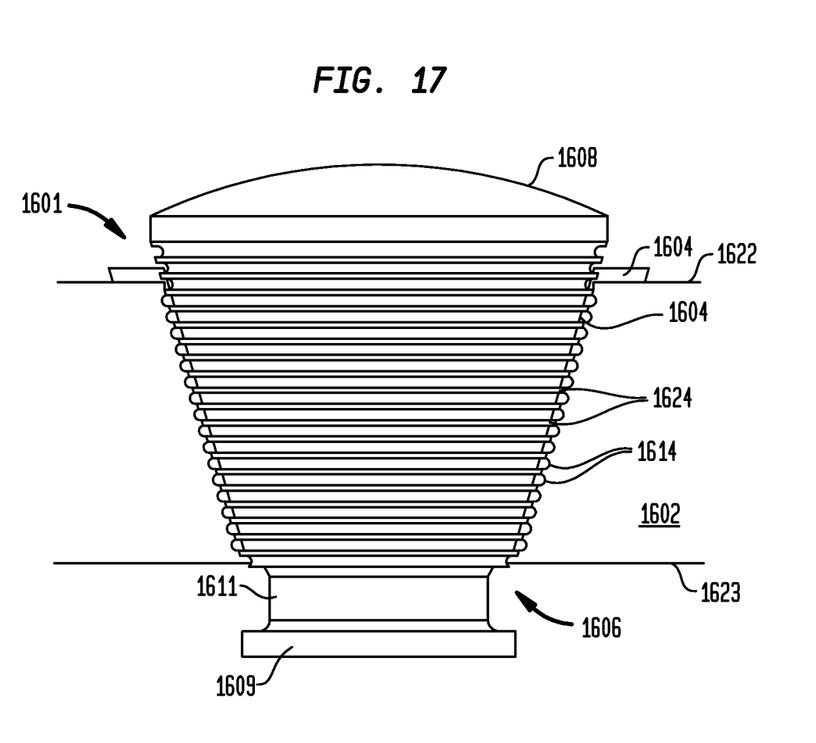
FIG. 17 is a side cross-sectional view of the pin inserted into the bone plate shown in FIG. 16.

FIGS. 16 and 17 depict a pin 1601 and bone plate 1602 in accordance with another embodiment of the present invention. Pin 1601 comprises head 1608, a shaft 1609, and a neck 1611. Both head 1608 and shaft 1609 are depicted as being partially disposed within a plate hole 1606. The outer diameter of shaft 1609 is substantially the same as the portion of plate hole 1606 near a lower surface 1623 of bone plate 1602. Plate hole 1606 is of a tapered configuration, having a tapered wall 1621 connecting upper surface 1622 and lower surface 1623. Plate hole 1606 has a smaller diameter nearer to lower surface 1623 and a larger diameter nearer to an upper surface 1622 of bone plate 1602. Tapered wall 1621 includes plate hole ridges 1614, which may be in the form of concentric rings or a continuous spiral thread. Head 1608 contains a plurality of pin head ridges 1624 similar in nature to bone plate hole ridges 1614. Pin head ridges 1624 may also be comprised of a plurality of concentric rings or a continuous spiral thread. About head 1608 and pin head ridges 1624 is disposed a polymer component 1604, in this case a coating. When pin 1601 is inserted through plate hole 1606 via a force F, an ultrasonic energy US is applied which melts polymer component 1604 which then fills the space between head 1608 and tapered wall 1621. As polymer component 1604 hardens or re-solidifies after insertion, plate hole ridges 1614 and pin head ridges 1624 effectively anchor polymer component 1604 to its hardened location, thereby substantially preventing movement of head 1604 relative to bone plate 1602. Plate hole ridges 1614 and pin head ridges 1624 aid in maintaining the position achieved by the hardened polymer component 1604. Head 1608 may be designed such that, when fully inserted into bone plate 1602, it does not project above upper surface 1622 of bone plate 1602. Alternatively, it may be desirable for a portion of head 1608 to extend beyond upper surface 1622.

FIG. 17 depicts head 1608 in a substantially fully inserted position within plate hole 1606. Polymer component 1604 is disposed between plate hole ridges 1614 and pin head ridges 1624 to secure head 1608 to tapered wall 1621 of plate hole 1606 through the re-solidified polymer component 1604. Due to the decreasing space between head 1608 and plate hole 1606 during insertion, a portion of polymer component 1604 may run onto upper surface 1622 and may then be removed.

According to a further embodiment, in order to more securely anchor a head of a pin to a plate hole of the present invention, it is contemplated that either or both of the head of the pin and the plate hole include lateral holes or grooves. In one embodiment, the bone plate includes one or more lateral holes or grooves that extend radially into the bone plate from the plate hole. In another embodiment, the pin head includes one or more lateral holes or grooves that extend into the head of the pin along at least a portion of its surface. Such lateral holes or grooves allow the polymer component, when melted, to become disposed within the lateral holes or grooves in order to further secure the head of the pin to the plate hole after re-solidification of the polymer component.

It is noted that polymer component according to any of the embodiments of the present invention may be able to yield slightly relative to the more rigid materials which comprise the pin and the bone plate. This allows for slight movement between the pin and the bone plate as the adjacent bone and/or tissue heals.

Although the invention herein has been described with reference to particular embodiments, it is to be understood that these embodiments are merely illustrative of the principles and applications of the present invention. It is therefore to be understood that numerous modifications may be made, and are encouraged to be made, to the illustrative embodiments without departing from the spirit and scope of the present invention as defined by the appended claims.

The invention claimed is:

1. A method of implanting a bone plate system comprising the steps of:
   positioning a device against an exterior surface of a bone, the device having at least one hole formed therethrough;
   inserting a member through the at least one hole and into the bone;
   providing a polymer component between at least the member and the device; and
   melting the polymer component through an application of energy.

2. The method of claim 1 wherein the step of melting includes applying ultrasonic energy.

3. The method of claim 2 wherein the step of inserting includes applying a driving force to the member.

4. The method of claim 3, wherein the step of melting is performed simultaneously with the step of inserting.

5. The method of claim 1, further comprising a step of pre-drilling a hole in the bone.

6. The method of claim 5, wherein the step of pre-drilling includes using a drill guide.

7. The method of claim 5, wherein the step of pre-drilling includes using the device as a drill guide.

8. The method of claim 1 wherein the member comprises a self-tapping screw, and wherein the step of inserting includes creating a bone hole through the insertion of the self-tapping screw.

9. The method of claim 1, further comprising a step of allowing the polymer component to re-solidify to form a bond between the device and the member.

10. A method of implanting a bone plate system comprising the steps of:
   positioning a device adjacent to a bone, the device having at least one hole formed therein;
   inserting a member through the at least one hole and into the bone;
   providing an annular polymer ring between at least the member and the device; and
   melting the polymer ring through an application of energy.

11. The method of claim 10, further comprising a step of inserting a shaft of the member through an aperture defined by the polymer ring.

12. The method of claim 10, wherein the polymer ring is positioned about a head of the member.

13. The method of claim 12, wherein the polymer ring is bonded with the head of the member by applying ultrasonic energy to the member prior to the step of inserting the member through the at least one hole.

14. The method of claim 10, further comprising a step of modifying an exterior surface of the polymer ring through machining.

15. The method of claim 1, wherein the step of providing the polymer component includes providing the polymer component on at least a portion of a shaft of the member, and further comprising a step of allowing the polymer component to re-solidify to form a bond between the member and the bone.

16. The method of claim 15, wherein the step of melting allows the polymer component to substantially fill at least a space between the member and the bone.

17. The method of claim 1, wherein the step of melting allows the polymer component to substantially fill at least a space between the member and the device.

18. The method of claim 1, further including repeating the group of steps of inserting, providing, and melting one or more times for one or more respective additional members.

19. The method of claim 1, wherein the step of inserting includes inserting the member such that it directly contacts the bone.

20. A method of implanting a bone plate system comprising the steps of:
   positioning a device adjacent to a bone, the device having at least one hole formed therein;
   inserting a member having a polymer component disposed thereon through the at least one hole and into the bone;
   coating the member with the polymer component prior the step of inserting the member;
   applying energy to melt the polymer component; and
   allowing the polymer component to re-solidify to form a bond between the member and the bone.

21. The method of claim 20, wherein the step of applying includes applying ultrasonic energy.

22. The method of claim 20, further comprising a step of allowing the polymer component to re-solidify to form a bond between the device and the member.

23. A method of implanting a bone plate system comprising the steps of:
   positioning a device adjacent to a bone, the device having at least one hole formed therein;
   inserting a member through the at least one hole and into the bone;
   providing a polymer component between at least the member and the device; and
   forming a bond between the device and the member by melting the polymer component through the application of energy and allowing the polymer component to re-solidify.

* * * * *